United States Patent [19]

Potoski

[11] Patent Number: 4,458,077
[45] Date of Patent: Jul. 3, 1984

[54] HETEROCYCLIC ANTI-ULCER AGENTS
[75] Inventor: John R. Potoski, Pottstown, Pa.
[73] Assignee: American Home Products Corporation, New York, N.Y.
[21] Appl. No.: 443,423
[22] Filed: Nov. 22, 1982
[51] Int. Cl.³ .................. C07D 277/30; C07D 307/54; C07D 211/34
[52] U.S. Cl. .................................... 548/197; 546/231; 548/184; 548/185; 548/196; 549/479; 549/491; 549/496; 424/267; 424/270; 424/285
[58] Field of Search ............... 548/184, 185, 196, 197; 546/231; 549/496, 491, 479

[56] References Cited

U.S. PATENT DOCUMENTS 4,128,658 12/1978 Price et al. .......................... 424/285
4,200,578 4/1980 Algieri et al. ....................... 548/193

Primary Examiner—Robert Gerstl
Attorney, Agent, or Firm—George Tarnowski

[57] ABSTRACT

Compounds of the formula $$Ar-(CH_2)_m-X-(CH_2)_n-ONHR$$

wherein R is

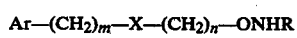

wherein
R¹ is hydrogen or lower alkyl;
X is O or CH₂;
m=0 or 1;
n=2 or 3; and
Ar is a moiety selected from the group

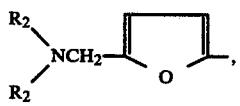

wherein R₂ is hydrogen or lower alkyl,

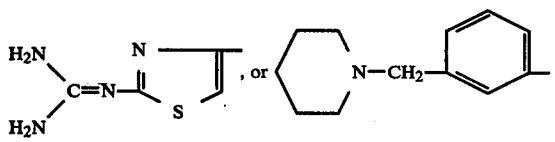

with the proviso that when Ar is

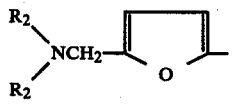

and X is CH₂, then R is other than

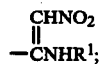

and the pharmacologically acceptable salts thereof have H₂-antagonist activity and activity in decreasing gastric acid secretions.

4 Claims, No Drawings

HETEROCYCLIC ANTI-ULCER AGENTS

This invention relates to new heterocyclic compounds having a selective action on $H_2$ histamine receptors and which inhibit gastric acid secretion.

It has been postulated that the physiologically active compound histamine, which occurs naturally within the animal body, is able to combine, in the course of exerting its activity, with certain specific receptors of which there are at least two distinct and separate types. The first has been named the $H_1$ receptor (Ash and Schild, Brit. J. Pharmac., 1966, 27, 427) and the action of histamine at this receptor is blocked (antagonized) by classical "antihistamine" drugs such as mepyramine (pyrilamine). The second histamine receptor has been named the $H_2$ receptor (Black et al., Nature, 1972, 236, 385) and the action of histamine at this receptor is blocked by drugs such as cimetidine. It is known that one of the results of the blockage of the action of histamine at the $H_2$ receptor is the inhibition of the secretion of gastric acid and a compound which possesses this ability is therefore useful in the treatment of peptic ulcers and other conditions caused or exacerbated by gastric acidity, including stress ulcers and gastrointestinal bleeding due to trauma.

The commercialization of cimetidine and subsequent follow-up pharmacological research in patients has demonstrated that cimetidine is a drug with limitations, such as short duration of action, anti-androgenic activity, and a tendency to cause confusional states in elderly patients. Obviously, much intensive research has been carried out to find improved $H_2$ antagonists. Indeed, selective $H_2$ antagonists having greater activity than cimetidine have been discovered. Among the better known new $H_2$ antagonists are ranitidine (disclosed in U.S. Pat. No. 4,128,658) having the structure:

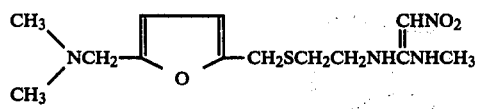

tiotidine (U.S. Pat. No. 4,165,378) having the structure:

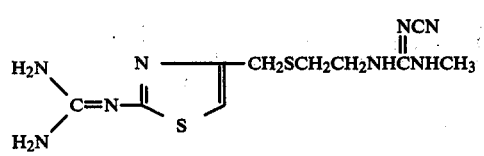

and compounds such as those disclosed in European Patent Application No. 24,510 having the structure:

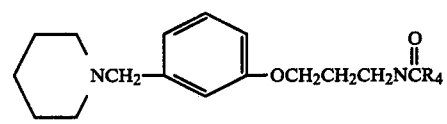

wherein $R_4$ is among others, hydrogen, methyl or methylol.

Also compounds such as those disclosed in U.S. Pat. No. 4,166,856 and having the structure:

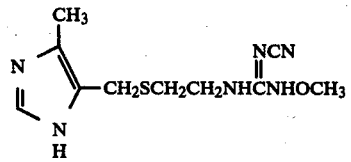

There has now been discovered a novel group of compounds, which exhibit $H_2$ receptor antagonist activity, and activity in reducing gastric acid secretions, and which have the following formula:

$$Ar-(CH_2)_m-X-(CH_2)_n-ONHR$$

wherein R is

wherein $R^1$ is hydrogen or lower alkyl, X is O or $CH_2$, m=0 or 1, n=2 or 3 and Ar is a moiety selected from the group

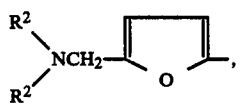

wherein $R^2$ is hydrogen or lower alkyl,

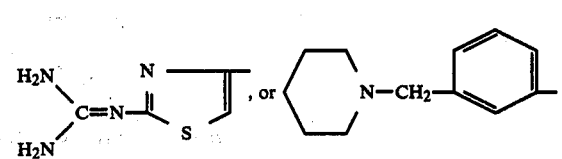

with the proviso that when Ar is

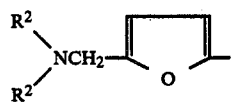

and

X is $CH_2$, then R is other than

and the pharmacologically acceptable salts thereof.

The compounds of the invention can be readily prepared by the following reaction scheme:

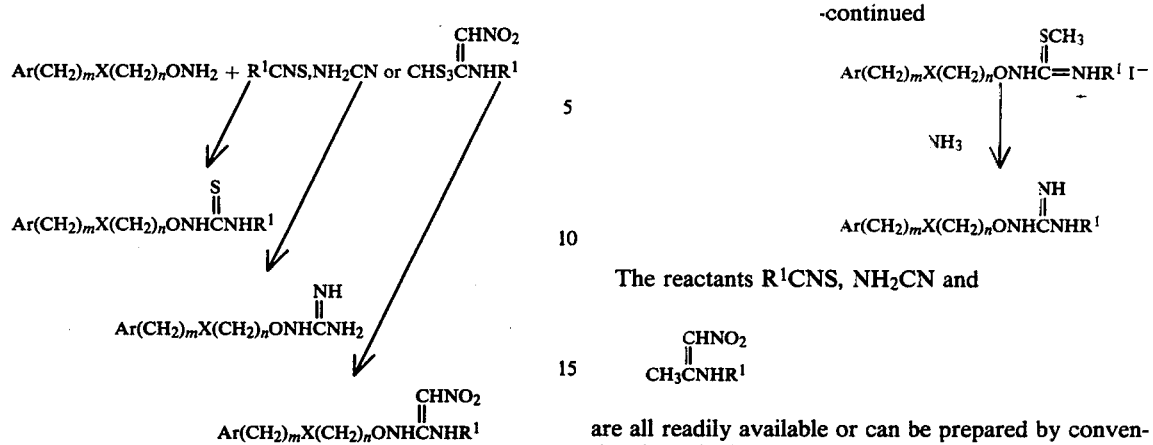

where Ar, $R^1$, X, m and n are as defined hereinbefore. Further, the methylthiourea compound can be converted to the guanidine derivative according to the following scheme:

-continued

The reactants $R^1CNS$, $NH_2CN$ and $$\underset{CH_3\overset{\|}{C}NHR^1}{CHNO_2}$$

are all readily available or can be prepared by conventional synthetic procedures. The aminooxyalkylheterocycles having the formula:

$$Ar(CH_2)_mX(CH_2)_nONH_2$$

can be obtained according to several similar preparative routes. Thus, the furan heterocycles can be prepared as follows:

Where $m=0$, $n=2$, $X=CH_2$

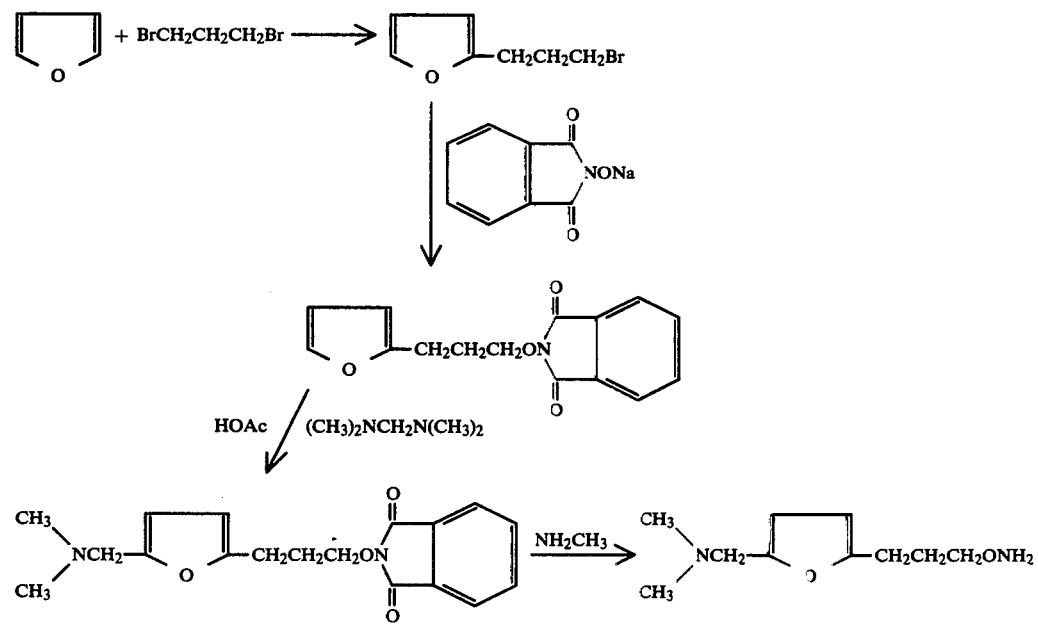

Where $m=1$, $n=2$, $X=0$

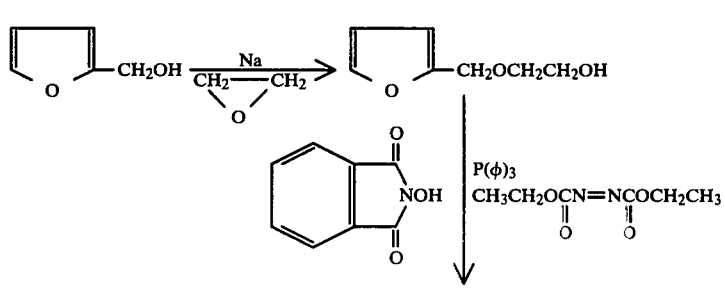

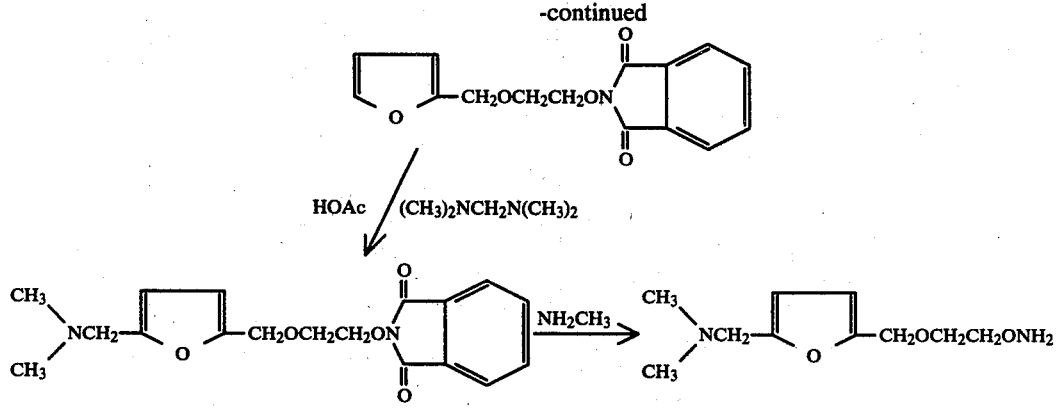

A similar stepwise incremental construction is carried out in the preparation of other amino-oxy intermediates. Thus, for example, the thiazole amino-oxy intermediates can be prepared as follows:

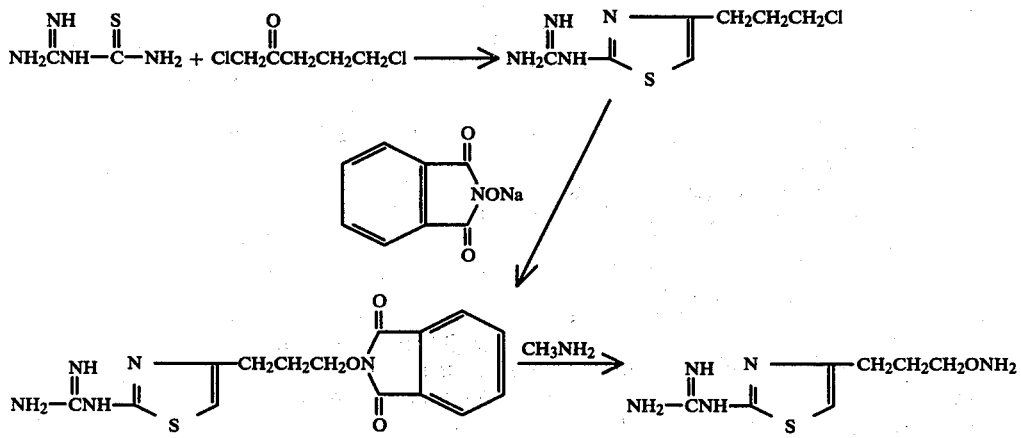

The compounds of the invention readily form pharmacologically acceptable salts with both inorganic and organic acids, such as hydrochloric, hydrobromic, sulfuric, nitric, phosphoric, acetic, maleic, fumaric, citric, oxalic, and the like.

The compounds of the invention have histamine $H_2$-blocking activity and activity in reducing gastric acid secretion, and can be used in the treatment of conditions where there is hypersecretion of gastric acid, such as in gastric and peptic ulceration, and other conditions caused or exacerbated by gastric acidity such as stress ulceration or gastric intestinal bleeding due to trauma.

The compounds of the invention can be administered orally or parenterally or by suppository, of which the preferred route is the oral route. They may be used in the form of the base or as a pharmacolgically acceptable salt. They will in general be associated with a pharmaceutically acceptable carrier or diluent, to provide a pharmaceutical composition.

The compounds of the invention can be administered in combination with other active ingredients, e.g. conventional antihistamines if required. For oral administration the pharmaceutical composition can most conveniently be in the form of capsules or tablets, which may be slow release tablets. The composition may also take the form of a dragee or may be in syrup form.

A convenient daily dose by the oral route would be of the order of 100 mg to 1.2 g per day, in the form of dosage units containing from 20 to 200 mg per dosage unit. A convenient regimen in the case of a slow release tablet would be twice or three times a day.

Parenteral administration may be by injections at intervals or as a continuous infusion. Injection solutions may contain from 10 to 100 mg/ml of active ingredient.

The histamine $H_2$-antagonist activity of the compounds of the invention may be demonstrated by the ability of the compounds to inhibit the histamine-induced positive chronotropic response in the spontaneously beating right atrium of the guinea pig heart, and the gastric acid secretion activity is demonstrated in the modified Shay procedure of pylorus ligation for the study of rat gastric secretion. The results for some of the compounds of the invention in these procedures is presented at the end of the following examples, which will serve to illustrate the present invention.

EXAMPLE 1

N-[2-[[[5-[(dimethylamino)methyl]-2-furanyl]methyl]-thio]ethoxy]-N'-methyl-2-nitro-1,1-ethenediamine, ethanedioate A. To a stirred solution of furfuryl mercaptan (1.14 g, 0.10 mole) in 15 ml of dimethylformamide under a nitrogen atmosphere is added 0.50 g (0.0104 mole) of 50% sodium hydride. The mixture is stirred for ½ hour. A solution of 2-bromoethoxyphthalimide (2.7 g, 0.010 mole) in 10 ml of dimethylformamide is added while cooling the mixture. The mixture is stirred at 25° for ½ hour and then at 40° for 1 hour. The reaction mixture is poured into water and the aqueous mixture is extracted with ethylacetate, dried and concentrated. The residue is chromatographed on 360 g of silica gel. Elution with a solution of 20% ethyl acetate in hexane gives after concentration of the eluate, 1.73 g of crystalline product with mp 40°-43°.

Analysis for: $C_{15}H_{13}NO_3S$, Calculated: C, 59.39; H, 4.31; N, 4.61, Found: C, 59.18; H, 4.34; N, 4.59.

B. A solution of the product of A. above (9.8 g), dimethylamine hydrochloride (3.2 g) and formalin (3.1 ml) in 45 ml of acetic acid is heated on a steam bath for 8 hours and then concentrated. The residue is dissolved in water, basified with sodium hydroxide and extracted with ethyl acetate. The extracts are dried and concentrated to give an oil which is chromatographed on 1 kg of silica gel. Elution with 2-3% methanol in methylene chloride gives after concentraion of suitable fractions, 4.9 g of product as an oil of suitable purity for the next transformation.

NMR: δ2.3 [6H, (CH$_3$)$_2$N], δ6.15

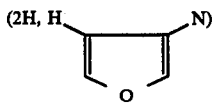

C. 5-[[[2-(amino-oxy)ethyl]thio]methyl]-N,N-dimethyl-2-furanmethanamine, bis(ethendioate)

A solution of the product of B. above (4.9 g) and 6 ml of 40% aqueous methylamine in 60 ml of ethanol is stirred at 25° for 1 hour and then concentrated. The residue is treated with ether and filtered. The filtrate is concentrated to give an oil which is chromatographed on 475 g of silica gel. Elution with 5% and 10% methanol in methylene chloride gives, after concentration of the suitable fractions, 1.701 g of product as an oil. Treatment of 0.50 g of this oil with 0.50 g of oxalic acid in ethanol gives 0.620 g of bis oxalate salt of the desired product with mp 105°-110° C.

Analysis for: $C_{10}H_{18}N_2O_2·2C_2H_2O_4$, Calculated: C, 40.97; H, 5.40; N, 6.83. Found: C, 41.11; H, 5.44; N, 6.61.

D. N-[2-[[[5-[(dimethylamino)methyl]-2-furanyl]methyl]-thio]ethoxy]-N'-methyl-2-nitro-1,1-ethanediamine, ethenedioate A mixture of the product of C. above (0.60 g, free base), 0.40 g of 1-methylamino-1-methylthio-2-nitroethylene and 15 ml of water is refluxed for 3½ hours. The resulting solution is concentrated and the residue is chromatographed on 175 g of silica gel. Elution with 2.5% methanol in methylene chloride gives, after concentration of the suitable fractions, 0.37 g of product as an oil. The oil is dissolved in ethanol and treated with 0.10 g of oxalic acid, diluted with ether and allowed to stand. Filtration gives 0.255 g of the oxalic acid salt of the product as a white powder with mp 63°-65° C.

Analysis for: $C_{13}H_{22}N_4O_4S·C_2H_2O_4$, Calculated: C, 42.85; H, 5.75; N, 13.33, Found: C, 42.97; H, 5.53; N, 13.59.

EXAMPLE 2

N-[2-[[5-[(dimethylamino)methyl]-2-furanyl]methoxy]ethoxy]-N'-methyl-2-nitro-1,1-ethenediamine, ethanedioate A. In a teflon lined steel bomb, under a nitrogen atmosphere, there is placed 61 g of furfuryl alcohol and 0.6 g of sodium. When the sodium is all dissolved, the bomb is cooled on an ice bath and 9.0 g of ethylene oxide is added to it. The bomb is then sealed and heated to 75° in an oil bath for 3 hours. After cooling, the reaction mixture is treated with 1.6 ml of acetic acid and fractionated through a Vigoreaux column to give 15.2 g of product with b-p. 116°-118° at 18 mm. This product is of sufficient purity for the next step.

B. To a stirred solution of the product of A. above (3.4 g, 0.221 mole), N-hydroxyphthalimide (36.1 g, 0.221 mole) and triphenylphosphine (58.0 g, 0.221 mole) in 750 ml of dry tetrahydrofuran cooled to 10° in an ice bath, is added 38.5 g (0.221 mole) of diethylazodicarboxylate. The temperature rises to 30°-35° and the reaction solution is allowed to stir at 25° overnight. The solution is concentrated and the residue is chromatographed on 1.5 kg of silica gel. Elution with 2% hexane in methylene chloride, gives on concentration of the fractions, 50 g of oil which crystallizes. Recrystallization from ethyl acetate-hexane gives 36.5 g of pure product. The analytical sample had m.p. 70°-72°.

Analysis for: $C_{15}H_{13}NO_5$, Calculated: C, 62.76; H, 4.56; N, 4.88, Found: C, 62.39; H, 4.65; N, 4.81.

C. A solution of the product of B. above (35.6 g, 0.124 mole) and N,N,N',N'-tetramethyldiaminomethane (12.66 g, 0.0124 mole) in 100 ml of acetic acid is heated to 50°-55° for 4½ hours. The solution is concentrated and the residue is dissolved in methylene chloride, washed with dilute aqueous bicarbonate and dried. This solution is concentrated to give 45 g of the product as an oil which is suitable for use in the next step.

NMR: δ2.3 [6H, s, (C$\underline{H}_3$)$_2$N], δ6.25

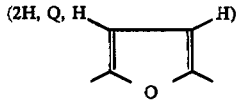

D. 5-[[[2-(aminooxy)ethoxy]methyl]-N,N-dimethyl-2-furanmethanamine.

By using the same procedure desired in Example 1C, from 4.5 g of the product in C. above, there is obtained 1.85 g of aminooxy product which is suitable for use in further transformations.

NMR: δ2.25 [6$\underline{H}$,s,(CH$_3$)$_2$N], δ6.2

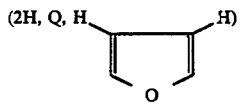

E. N-[2-[[5-[(dimethylamino)methyl]-2-furanyl]-methoxy]ethoxy]-N'-methyl-2-nitro-1,1-ethenediamine, ethanedioate By using the same procedure described in Example 1D, from 1.0 g of the product from D. above, there is obtained 0.96 g of the oxalic acid salt of the desired product with m.p. 106°-109°.

Analysis for: $C_{13}H_{22}N_4O_5$, Calculated: C, 44.55; H, 5.98; N, 13.86, Found: C, 44.77; H, 6.12; N, 13.65.

EXAMPLE 3

N-[3-[5-[(dimethylamino)methyl]-2-furanyl]propoxy]-N'-methyl-2-nitro-1,1-ethenediamine, ethanedioate A. To a stirred solution of butyllithium (500 ml, 1.6 molar in hexane) under a nitrogen atmosphere and cooled to −30° is added 700 ml of dry tetrahydrofuran and 51.1 g of furan. The solution is stirred for 1 hour at −30° then cooled to −60°. At this temperature a cold (−25°) 436 g portion of 1,3-dibromopropane is added.

The reaction is allowed to come to 25° and stir overnight. The reaction mixture is poured into a mixture of 300 ml of ether and 300 ml of water. The organic layer is separated and the aqueous layer is further extracted with ether. The combined organic layers are dried, concentrated and distilled through a Vigoreaux column to give 70.2 g of the desired product with bp. 50°–52° at 0.4 mm. This product is of suitable purity for further transformation.

B. To a stirred suspension of 1.28 g (0.027 mole) of sodium hydride (50%, nujol) in 40 ml of dimethylsulfoxide under nitrogen atmosphere is added 4.32 g (0.027 mole) of N-hydroxyphthalimide as a slurry in 50 ml of dimethylsulfoxide. The mixture is stirred for 1 hour. To the resultant deep red mixture is added 5.0 g (0.027 mole) of the product from A. above in 10 ml of dimethylsulfoxide. The mixture is stirred overnight at 40°, cooled to 25° and poured into water. A white solid forms which is filtered. The solid is dissolved in 30 ml of ethyl acetate and 25 ml of hexane is added. A white solid crystallizes which is filtered. The filtrate is chromatographed on 365 g of silica gel. Elution with 20% ethyl acetate in hexane gives after concentration of the suitable fractions, 3.3 g of product as a white solid with m.p. 81°–83°.

C. By using the same procedure as that described in Example 2C, from 3.3 g of the product from B. above, there is obtained 3.35 g of the desired product as an oil suitable for further transformations.

NMR: δ2.3 [6H,s,(C$\underline{H}_3$)$_2$N-], δ6.15

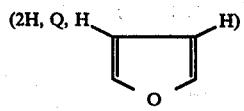

(2H, Q, H̲ ̲H̲)
O

D. 5-[3-(aminooxy)propyl]-N,N-dimethyl-2-furanmethanamine

By using the same procedure described in Example 1C, from 3.3 g of the product from C. above there is obtained 1.3 g of aminooxy product which is suitable for use in further transformations.

E. N-[3-[5-[(dimethylamino)methyl]-2-furanyl]propoxy]-N'-methyl-2-nitro-1,1-ethenediamine, ethanedioate By using the same procedure described in Example 1D. from 1.25 g of the product from D. above, there is obtained 1.39 g of the oxalic salt of the desired product with m.p. 90°–95°.

Analysis for: $C_{13}H_{22}N_4O_4C_2H_2O_4$, Calculated: C, 46.39; H, 6.23; N, 14.43, Found: C, 46.13; H, 6.06; N, 14.10.

EXAMPLE 4

N-[2-[[5-[(dimethylamino)methyl]-2-furanyl]methoxy]ethoxy]-N'-methyl-thiourea, ½ hydrate A solution of 1.1 g (0.0050 mole) of the product of Example 2D, and 0.40 g of methylisothiocyanate in 25 ml of methylene chloride is refluxed for 5 hours then allowed to stand overnight. The reaction solution is concentrated and the residue obtained is chromatographed on 125 g of silica gel. Elution with 5% methanol in methylene chloride gives, after concentration of the suitable fractions, 0.634 g of oil which crystallizes. Recrystallization of the oil from ethylacetate-hexane gives 0.24 g of product as a white solid with m.p. 77°–79°.

Analysis for: $C_{12}H_{21}N_3O_3S\cdot\frac{1}{2}H_2O$, Calculated: C, 49.12; H, 7.44; N, 14.32, Found: C, 49.14; H, 7.01; N, 13.72.

EXAMPLE 5

[4-[3-[[[1-(methylamino)-2-nitroethenyl]amino]oxy]propyl]-2-thiazolyl]guanidine

A. To a stirred solution of 1,5-dichloro-2-pentanone (9.0 g, 0.058 mole) in 75 ml of acetone is added amidinothiourea (6.2 g, 0.052 mole). The mixture is stirred for 5 hours and allowed to stand overnight. The mixture is concentrated and the residue dissolved in ethanol and the ethanol solution is treated with ether. The hydrogen chloride salt of the product precipitates from this solution. Filtration of the mixture gives 8.4 g of salt with m.p. 107°–108°. Further recrystallization from ethanol ether gives a salt with a m.p. 109°–111°. Conversion of this salt to the free base by usual methods gives a base with m.p. 82°–3° on recrystallization from ether-hexane.

B. To a stirred suspension of 2.63 g (0.066 mole) of sodium hydride (60% nujol) in 100 ml of dimethylsulfoxide under a nitrogen atmosphere is added 10.7 g (0.066 mole) of N-hydroxyphthalimide as a slurry in 100 ml of dimethylsulfoxide. The mixture is stirred for 1 hour. To the resultant red mixture is added the free base of the product described in A. above. The reaction mixture is heated to 80° for 3 hours then is poured into water. The aqueous mixture is extracted 5 times with ethyl acetate. The combined extracts are dried and concentrated to give an oil residue. This is dissolved in ethanol, treated with hydrogen chloride and diluted with ether. The hydrogen chloride salt of the product crystallizes from this solution. Filtration gives 10.5 g with m.p. 215°–218°.

Analysis for: $C_{15}H_{15}N_5O_2SHCl$, Calculated: C, 47.18; H, 422; N, 18.34, Found: C, 47.13; H, 4.28; N, 18.29.

C. [2-[4-[3-(aminooxy)propyl]thiazolyl]]guanidine

To a suspension of 5.9 g of the hydrochloride salt of the product described in B. above in 90 ml of ethanol is added 12 ml of 40% aqueous methylamine. The undissolved salt immediately dissolves. After 4 hours of stirring at 25° a white solid begins to precipitate. After standing overnight, filtration gives 1.97 g of desired product as the free base. The base is dissolved in ethanol treated with hydrogen chloride and the solution diluted with ether. The dihydrogenchloride salt of the product precipitates. Filtration gives 1.6 g of salt with m.p. 182°–185°.

Analysis for: $C_7H_{17}N_5OS2HCl$, Calculated: C, 29.17; H, 5.25; N, 24.30, Found: C, 29.42; H, 5.21; N, 24.21.

D. [4-[3-[[[1-(methylamino)-2-nitroethenyl]amino]oxy]propyl]-2-thiazolyl]guanidine By using the same procedure described in Example 1D. from 2.0 g of the product base obtained in C. above, there is obtained 0.47 g of the dihydrogen chloride salt of the desired product with m.p. 144°–146°.

Analysis for: $C_{10}H_{17}N_7O_3S2HCl$, Calculated: C, 30.93; H, 4.93; N, 25.25, Found: C, 30.57; H, 4.85; N, 24.70.

EXAMPLE 6

The guniea pig heart atrium test is carried out as follows:

A guinea pig right atrium is suspended at 1 g. tension (isometric) in a thermostatically controlled (32° C.) tissue bath (10 ml) containing oxygenated (95% $O_2$; 5% $CO_2$) Krebs-Haenseleit buffer (pH 7.4). The tissue is allowed to stabilize over 1 hour. Individual contractions are recorded with a force-displacement transducer through a strain gauge coupler. A control dose-response curve to histamine in the above described tissue bath is obtained after which the tissue is washed 3 times and allowed to re-equilibrate to basal rate. The test compound is added to the tissue bath at the desired final concentration. Thirty minutes after addition of the compound, a fresh histamine dose response curve is again obtained. Then the response to histamine in the presence of antagonist is compared to the histamine control response. This procedure is repeated, using fresh tissues, for each concentration of antagonist tested. The result is expressed as the apparent dissociation constant ($pA_2$) of the $H_2$ antagonist as determined by standard procedures. Cimetidine is used as the standard for this test.

The results for a series of compounds of the invention are as follows:

| Compound of Example No. | $pA_2$ Value |
| --- | --- |
| 2 | 5.04 |
| 4 | 5.90 |
| 5 | $1.083 \times 10^{-7}$* |

*This value is the $K_B$ value for the compound tested, and the $K_B$ differs from the $A_2$ value only by the fact that the $A_2$ value reflects the results of three experiments, while the $K_B$ value represents the result of only one experiment.

The results show that the compounds of the invention exhibit $H_2$ antagonist activity.

EXAMPLE 7

The procedure for testing gastric secretion in the rat, a modification of the procedure of Shay et al., Gastroenterology, 26, 906–13 (1954) is carried out as follows:

Male Charles River rats weighing 200–300 grams are deprived of food but not water for 24 hours prior to use. Water is, however, withheld during the experiment. The rats are weighed, anesthetized, and the pylorus ligated according to the method of Shay et al. Treatment or vehicle control is then administered interduodenally (i.d.). Rats are housed 2/cage and sacrificed with $CO_2$ four hours after ligation. The stomachs are removed, rinsed, and contents emptied into a graduated centrifuge tube. The tubes are centrifuged for 20 minutes at 2,000 RPM and the volume of gastric juice recorded. Any samples obviously contaminated by feces, food or hemolysis are eliminated. An aliquot of each is frozen for later analysis of $Na^+$, $K^+$ and $Cl^-$ concentration. The pH is measured and 1 ml. of gastric juice is titrated with 0.1N NaOH to a pH of 7.0–7.4. Titrable acid output is calculated in microequivalents and the percent inhibition of acid output is calculated as follows:

% Inhibition of Acid Output =

$$\frac{\text{Acid Output (control)} - \text{Acid Output (Drug)}}{\text{Acid Output (control)}} \times 100$$

The test result for a compoundd of the invention is as follows:

| Compound of Example No. | Dose (mg/kg) | % Inhibition |
| --- | --- | --- |
| 5 | 32 | 72 |

The results show the compound of the invention to have significant activity in inhibiting gastric acid secretion.

What is claimed is:

1. A compound having the formula:

$$Ar-(CH_2)_m-X-(CH_2)_n-ONHR$$

wherein R is $$-\overset{\overset{S}{\|}}{C}NHR^1, \quad -\overset{\overset{CHNO_2}{\|}}{C}NHR^1 \text{ or } -\overset{\overset{NH}{\|}}{C}NHR^1,$$

wherein
$R^1$ is hydrogen or lower alkyl;
X is O or $CH_2$;
m=0 or 1;
n=2 or 3; and,
Ar is a moiety selected from the group

[structure: $R^2$-N(-$R^2$)-$CH_2$-furan-O-]

wherein $R^2$ is hydrogen or lower alkyl,

[structures: $H_2N$-C(=N-)-thiazole-$CH_2$- , or piperidine-N-$CH_2$-phenyl-]

with the proviso that when Ar is

[structure: $R_2$-N(-$R_2$)-$NCH_2$-furan-O-]

and X is $CH_2$, then R is other than $$-\overset{\overset{CHNO_2}{\|}}{C}NHR^1;$$

and the pharmacologically acceptable salts thereof.

2. The compound of claim 1, having the name N-[2-[[5-[(dimethylamino)methyl]-2-furanyl]methoxy]ethoxy]-N'-methyl-2-nitro-1,1-ethenediamine.

3. The compound of claim 1, having the name N-[2-[[5-[(dimethylamino)methyl]-2-furanyl]methoxy]ethoxy]-N'-methylthiourea.

4. The compound of claim 1, having the name [4-[3-[[[1-(methylamino)-2-nitroethenyl]amino]oxy]propyl]-2-thiazolyl]guanidine.

* * * * *